United States Patent [19]

Outlaw, III

[11] Patent Number: 5,323,901
[45] Date of Patent: * Jun. 28, 1994

[54] DISPOSABLE INFECTIOUS WASTE CONTAINER ASSEMBLY

[75] Inventor: Thomas J. Outlaw, III, Monroe, Conn.

[73] Assignee: B&D Molding Products Inc., Shelton, Conn.

[*] Notice: The portion of the term of this patent subsequent to Apr. 13, 2010 has been disclaimed.

[21] Appl. No.: 14,666

[22] Filed: Feb. 8, 1993

[51] Int. Cl.$^5$ .................................................. B65D 83/02
[52] U.S. Cl. ..................................... 206/366; 206/370
[58] Field of Search ................................. 206/366, 370

[56] References Cited

U.S. PATENT DOCUMENTS

| | | | |
|---|---|---|---|
| 3,057,506 | 10/1962 | Wetlesen | 220/17 |
| 4,715,498 | 12/1987 | Hanifl | 206/366 |
| 4,722,472 | 2/1988 | Bruno | 229/128 |
| 4,804,090 | 2/1989 | Schuh et al. | 206/366 |
| 4,809,850 | 3/1989 | Laible et al. | 206/366 |
| 4,826,073 | 5/1989 | Bruno | 229/128 |
| 4,828,107 | 5/1989 | Spencer | 206/366 |
| 4,869,366 | 9/1989 | Bruno | 206/370 |
| 4,903,832 | 2/1990 | Stewart | 206/366 |
| 4,911,294 | 3/1990 | Russo et al. | 206/366 |
| 4,955,477 | 9/1990 | Bruno | 206/366 |
| 4,972,950 | 11/1990 | Shillington | 206/366 |
| 5,046,613 | 9/1991 | Baudry et al. | 206/366 |
| 5,046,614 | 9/1991 | Torres et al. | 206/366 |
| 5,076,429 | 12/1991 | Patrick et al. | 206/370 |
| 5,080,251 | 1/1992 | Noack | 220/335 |
| 5,145,063 | 9/1992 | Lee | 206/366 X |
| 5,154,345 | 10/1992 | Shillington | 232/44 |
| 5,181,609 | 1/1993 | Spielmann et al. | 206/366 X |
| 5,201,417 | 4/1993 | Outlaw, III | 206/366 |

*Primary Examiner*—Paul T. Sewell
*Assistant Examiner*—BethAnne C. Cicconi
*Attorney, Agent, or Firm*—Ohlandt, Greeley & Ruggiero

[57] ABSTRACT

An infectious waste disposal system comprising an outer container assembly comprising a housing unit which comprises a front side wall, a rear side wall and a means for mounting the outer container assembly on a wall or any other such surface, an outer aperture disposed about the top of the housing unit, an access door disposed about the base of the housing unit and a means for locking the access door to the housing unit; and a removable inner container assembly disposed within the outer container assembly, the inner container assembly comprising a receptacle housing, an inner aperture with an inner elongated neck portion and an aperture closure means, the inner aperture being capable of providing access to the interior of the receptacle housing and the aperture closure means having a shape such that it can be removed from the inner container assembly, inverted and inserted into the inner elongated neck portion via the inner aperture such that infectious waste contained within the receptacle housing cannot escape through the inner aperture.

15 Claims, 8 Drawing Sheets

DISPOSABLE INFECTIOUS WASTE CONTAINER ASSEMBLY

The present invention relates generally to disposable infectious waste containers, and, more particularly, to containers which provide for the safe handling and disposal of potentially injurious or contaminated sharps, objects and wastes. These containers are especially useful in the disposing of scalpel blades, hypodermic needles and like devices which pose a risk of causing infection or even disease if an open wound is created by or exposed to such implement. They also provide for the safe disposal of sanitary napkins and the like.

BACKGROUND OF THE INVENTION

Disposable surgical tools, hypodermic needles, scalpel blades and other sharp implements require proper means for storing after use without risk of exposing medical personnel and patients to injury, infection or disease by improper handling, until proper disposal can be made. This is particularly true today with the rising concern of the spread of AIDS and Hepatitis B.

Although the AIDS disease is transmitted via the contacting of bodily fluids, Hepatitis B, it has been recently discovered, can be transmitted by covert percutaneous, i.e., by merely contacting the contaminated needle or implement. Recent studies have confirmed that Hepatitis B can also be transmitted by casual contact with dried blood such as that disposed on a sanitary napkin.

A few specially designed containers have been proposed for handling used needles and other sharps. See for example U.S. Pat. No. 4,869,366 (Bruno), which issued on Sep. 26, 1989, U.S. Pat. No. 4,826,073 (Bruno), which issued on May 2, 1989, U.S. Pat. No. 4,972,950 (Shillington), which issued on Nov. 27, 1990, and U.S. Pat. No. 4,722,472 (Bruno), which issued on Feb. 2, 1988. These containers are typically made out of metal, plastic or cardboard.

Other medical waste disposal containers are set forth in U.S. Pat. Nos. 5,080,251 (Noack), 5,076,429 (Patrick et al.), 5,046,614 (Torres et al.), 5,046,613 (Baudry et al.), 5,024,327 (Shillington), 4,955,477 (Bruno), 4,922,597 (Ikeda et al.), 4,903,832 (Stewart), 4,867,309 (Germain), 4,863,052 (Lambert), 4,848,570 (Gosciniak), 4,842,138 (Sandel et al.), 4,804,090 (Schuh et al.), 4,715,498 (Hanifl), 4,662,516 (Baker, Sr. et al.), 4,520,926 (Nelson), 4,494,652 (Nelson et al.), 4,454,944 (Shillington et al.), 4,453,648 (Harris et al.), and 4,520,926 (Nelson).

Although such specially designed devices provide adequate results under certain circumstances, they do suffer certain disadvantages. For example, conventional metal containers are extremely costly in terms of manufacturing cost, i.e., metal containers require welding, die cutting of parts, assembly and painting. The painting also causes various environmental concerns such as disposal of the solvents and air pollution. Cardboard containers are not waterproof and therefore cannot be transported interstate due to U.S. Department of Transportation regulations on shipment of hazardous or infectious waste. Conventional plastic containers are multi-piece devices which require costly assembly and multiple plastic molds for their manufacture. Some conventional plastic containers are designed in such a way that they cause the sharps to stand on end creating a hazardous environment for subsequent health care providers and disposal personnel.

Sanitary napkins are currently disposed of together with ordinary lavatory trash. However, this will probably not be permissible within the next few years, since researchers have recently discovered that Hepatitis B can be transmitted via casual contact with dried blood. Sanitary napkins will have to be disposed of in an environmentally safe manner and probably will be subjected to similar disposal regulations currently covering other infectious or hazardous wastes.

It is an object of the present invention to provide a novel disposal container assembly which overcomes the many disadvantages of the conventional devices. In particular, the present invention provides a single blow molded plastic disposable infectious waste container wherein the lid of the container is molded together with the container in a single mold. Thereafter, the lid is cut off from the container assembly so that it can be inverted and inserted into the elongated neck portion via the aperture to seal the medical waste within the container assembly. This single blow molded piece is extremely economical for the following reasons: (1) it is much less expensive to manufacture than conventional plastic or metal containers since it only necessitates the use of a single mold; and (2) it does not require any assembly after molding.

The present invention also provides many additional advantages which shall become apparent as described below.

SUMMARY OF THE INVENTION

An infectious waste disposal container assembly which comprises a receptacle housing, an aperture with an elongated neck portion and an aperture closure means. The aperture of the container assembly being capable of providing access to the interior of the receptacle housing. The aperture closure means having a shape such that it can be removed from the container assembly, inverted and inserted into the elongated neck portion via the aperture such that infectious waste contained within the receptacle housing cannot escape through the aperture.

A further object of the present invention is an infectious waste disposal system comprising: an outer container assembly comprising a housing unit, an outer aperture disposed about the top of the housing unit, and an access door disposed about the base of the housing unit; means for mounting the outer container assembly on a wall; and a removable inner container assembly disposed within the outer container assembly, the inner container assembly comprising a receptacle housing, an inner aperture with an elongated neck portion, and an aperture closure means, the aperture of the inner container assembly being capable of providing access to the interior of the receptacle housing and the aperture closure means having a shape such that it can be removed from the container assembly, inverted and inserted into the elongated neck portion via the inner aperture such that infectious waste contained within the receptacle housing cannot escape through the inner aperture.

The outer container assembly may preferably include integral mounting means, such as through holes, disposed about the side walls thereof such that the outer container assembly can be mounted directed to a wall or other surface without the need for an separate mounting means.

Other and further objects, advantages and features of the present invention will be understood by reference to the following specification in conjunction with the annexed drawings, wherein like parts have been given like numbers.

DESCRIPTION OF THE PREFERRED EMBODIMENTS

The present invention is directed to a single blow molded plastic disposable infectious waste container or insert, wherein the lid of the container is molded together with the receptacle housing and the aperture with elongated neck portion, and thereafter removed at an appropriate cut line. When the container is to be replaced, the previously removed lid is inverted and inserted into the elongated neck portion of the container via the aperture to seal the contents within the receptacle housing. It is preferable that the lid be snapped into place prior to removal of the inner container assembly from an outer container assembly; thereby protecting the operator from contact with the contents thereof caused by spills which can occur if the container is removed prior to sealing.

As is demonstrated in the attached drawings, the infectious waste container assembly is preferably used in a disposal system which includes an outer container assembly with locking means, an infectious waste or inner container assembly which is housed within the outer container assembly, and, optionally, a means for mounting the outer container assembly on a wall or other such surface. This disposal system provides adequate security against unauthorized removal of the infectious waste container assembly, while also providing an inexpensive and safe means for temporarily storing infectious waste products such as sharps in hospital and other medical treatment facilities. Other infectious waste products such as sanitary napkins can also be disposed therein.

Figure 1:
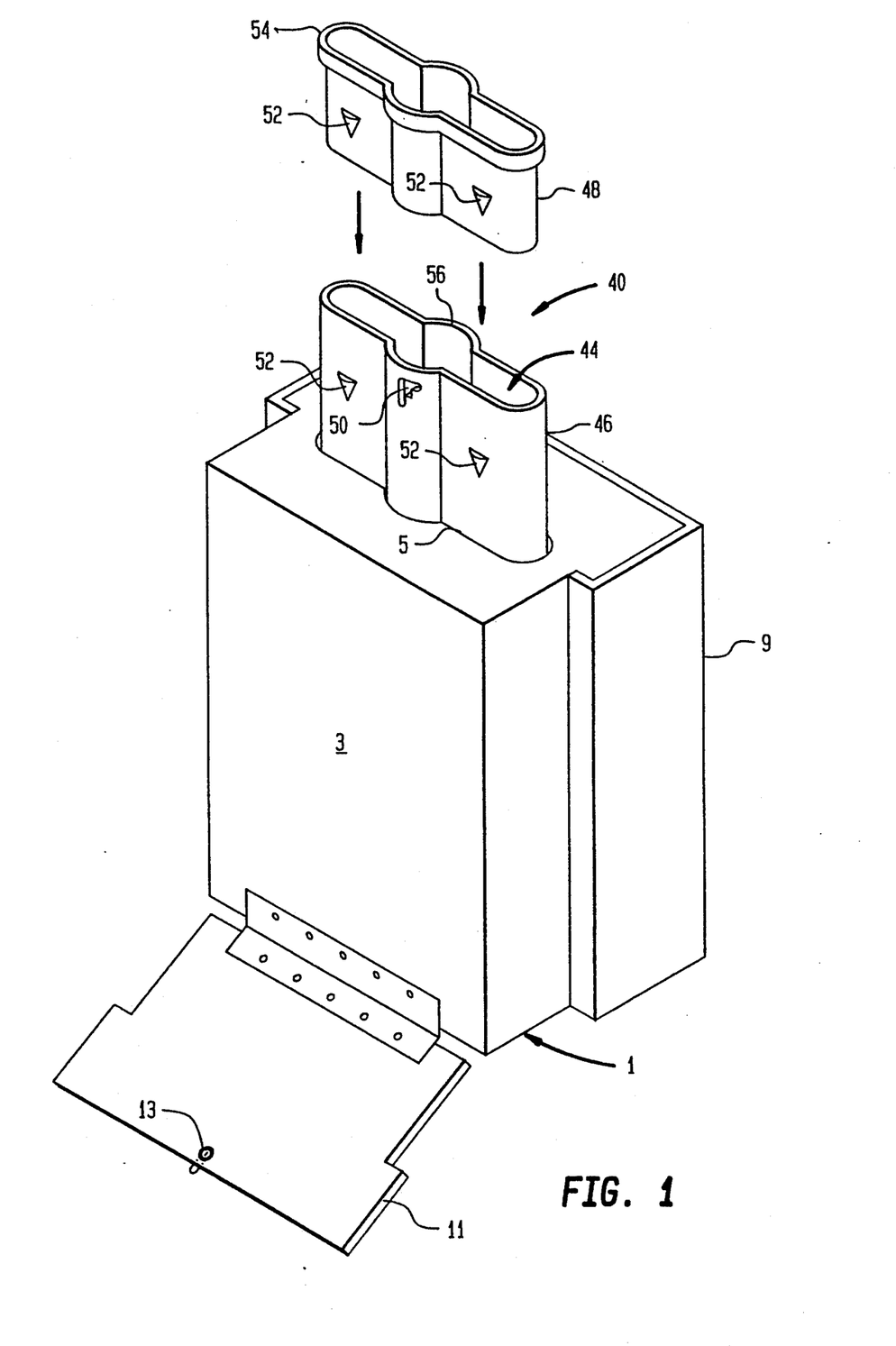
FIG. 1 is a schematic representation of a top-front perspective view of an infectious waste disposal system in accordance with the present invention, wherein the inner aperture and elongated neck portion of the inner container assembly protrudes through the outer aperture of the outer container assembly.

The present invention can best be described by referring to the attached drawings, wherein FIG. 1 depicts an infectious waste disposal system. This infectious waste disposal system comprises an outer container assembly 1 having a housing unit 3 and an outer aperture 5 disposed about the top of housing unit 3, and an access door 11 disposed about the base of housing unit 3; means 9 for mounting outer container assembly 1 on a wall or other such surface; and a removable inner container assembly 40 disposed within outer container assembly 1 such that elongated neck portion 46 protrudes through aperture 5 and such that when access door 11 is completely open inner container assembly 40 falls through the hole created in bottom of outer container assembly 1.

Access door 11 preferably includes a locking device 13 which is securely connected to either mounting means 9 or a shelf, not shown, disposed within the rear wall of outer container assembly 1 when in the locked position.

Figure 2:
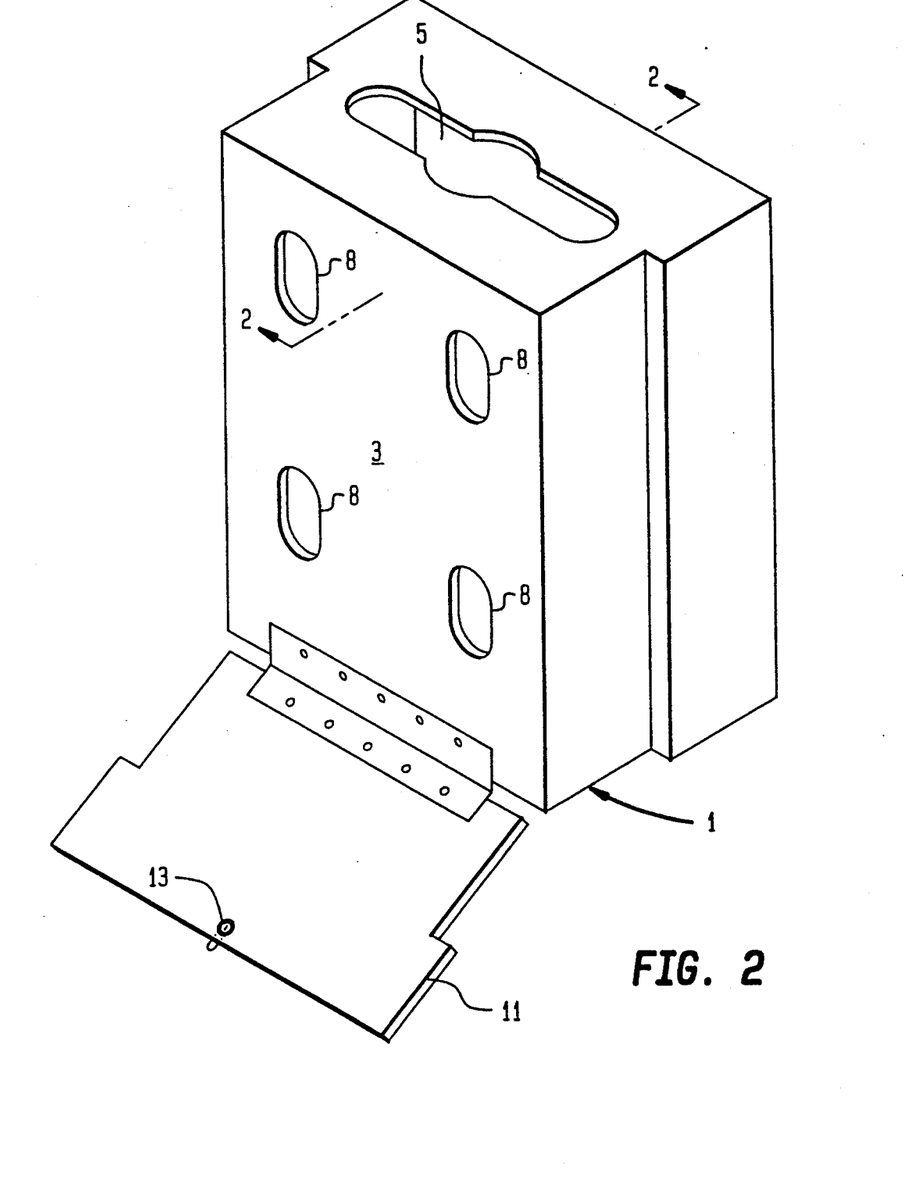
FIG. 2 is a schematic representation of a top-front perspective view of an outer container assembly in accordance with the present invention, wherein the access door of the outer container assembly is in the open position.
Figure 2A:
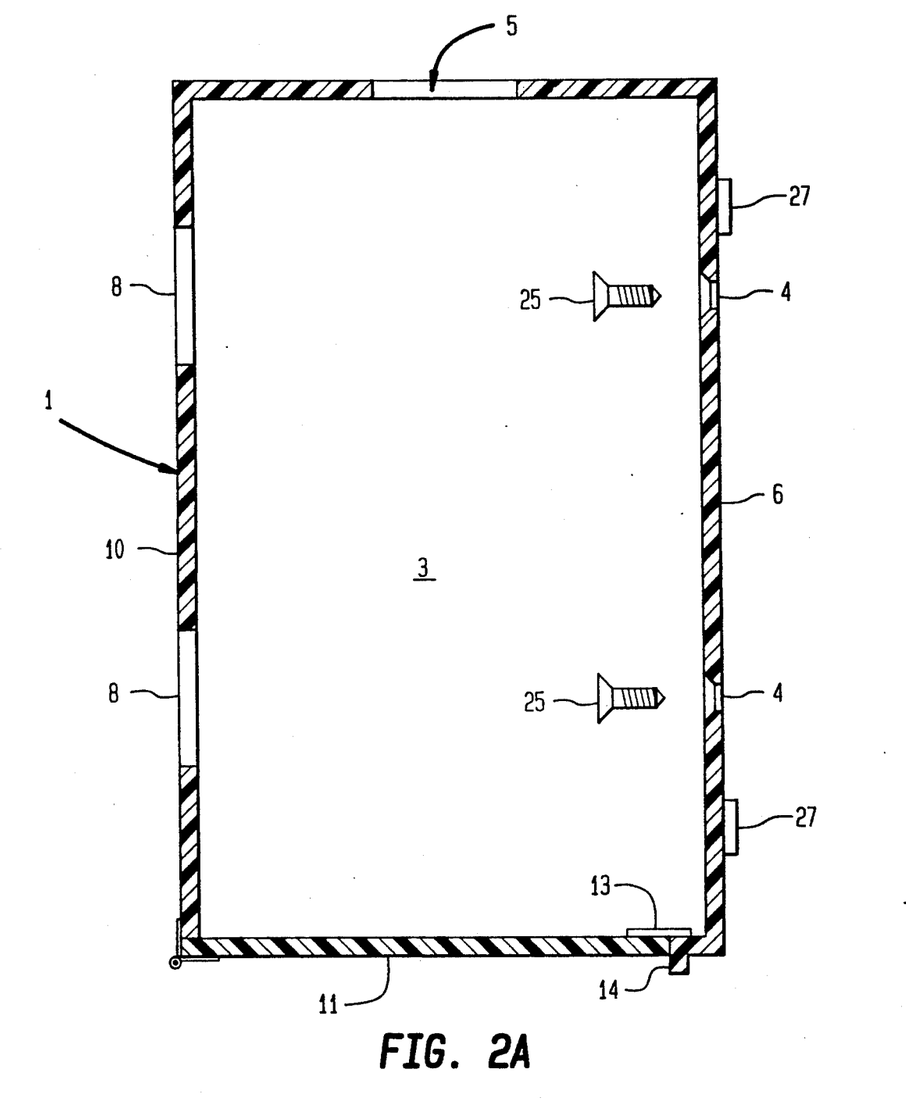
FIG. 2a is a cross-sectional view along line 2—2 of FIG. 2 showing another embodiment according to the present invention wherein through holes are disposed along the side walls thereof and the access door is in the closed position.
Figure 3:
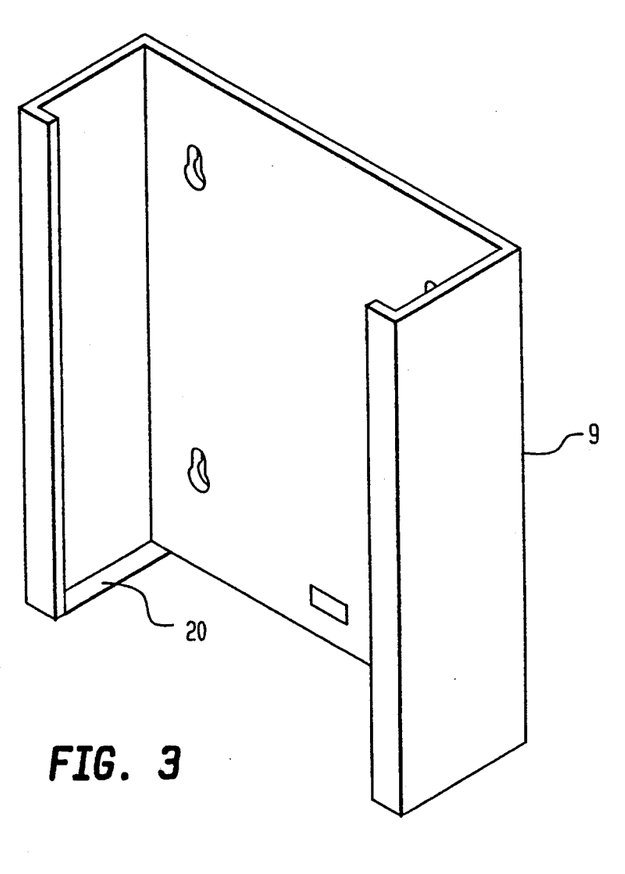
FIG. 3 is a schematic representation of a top-front perspective view of a mounting means in accordance with the present invention.

FIG. 2 depicts an outer container assembly 1 having an external shape which is capable of being slidingly mounted within the U-shaped metal or plastic bracket of the mounting means shown in FIG. 3. Optionally, outer container assembly 1 can be designed so that it may be mounted without the need for mounting means 9. FIG. 2a depicts a preferred embodiment wherein outer container assembly 1 preferably includes through holes 4 disposed about rear side wall 6 thereof such that outer container assembly 1 can by itself be mounted directed to a wall or other surface. Any type of acceptable means for securing outer container assembly 1 via through holes 4, such as screws 25 or counter sinks, are contemplated hereunder. For convenience, outer container assembly 1 should also include slots 8 disposed within front side wall 10 to permit access therethrough to holes 4 such that a means for securing or mounting outer container assembly 1 can be reached which a screwdriver or the like.

Alternatively the integral mounting means for securing outer container assembly 1 to an external wall or surface can be an adhesive 27 or the like affixed to the exterior surface of rear side wall 6 of housing unit 3. Still it is possible that the integral mounting means can be a integrated bracket or the like molded directing within outer container assembly 1.

When outer container assembly 1 is self mounted, access door 11 is locked by means of lock 13 being in contact with lock shelf 14. Preferably lock shelf 14 is formed directly within rear side wall 6 of outer container assembly 1.

As shown in FIG. 3, mounting means 9 is preferably a U-shaped metal or plastic bracket having a base portion 20 which is capable of permitting the inner container assembly to fall there through while simultaneously supporting the outer container assembly and which is open at the top such that outer container assembly can be readily removed therefrom. When access door 11 is in the locked position and securely connected to mounting means 9, the vertical movement of outer container assembly 1 is restricted since base portion 20 of mounting means 9 is disposed between access door 11 and housing unit 3.

Figure 4:
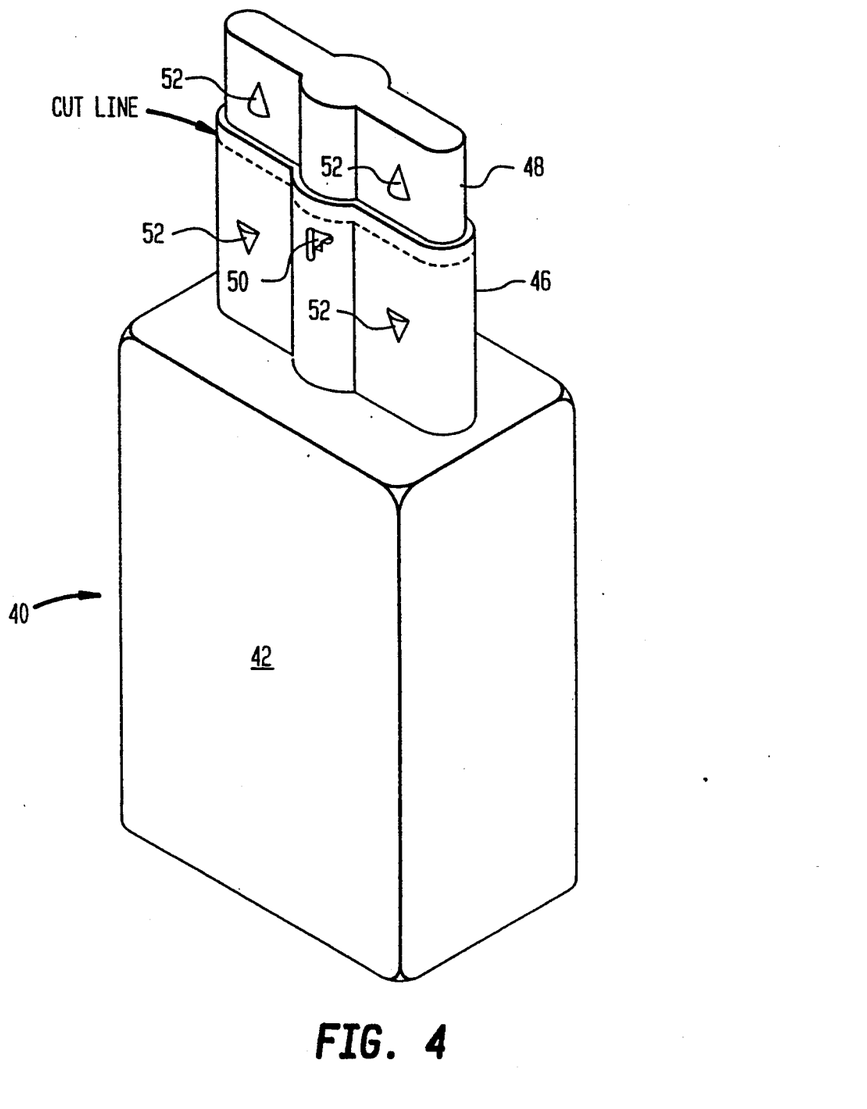
FIG. 4 is a schematic representation of a top-front perspective view of a blow molded inner container assembly prior to removal of the aperture closure means.
Figure 5:
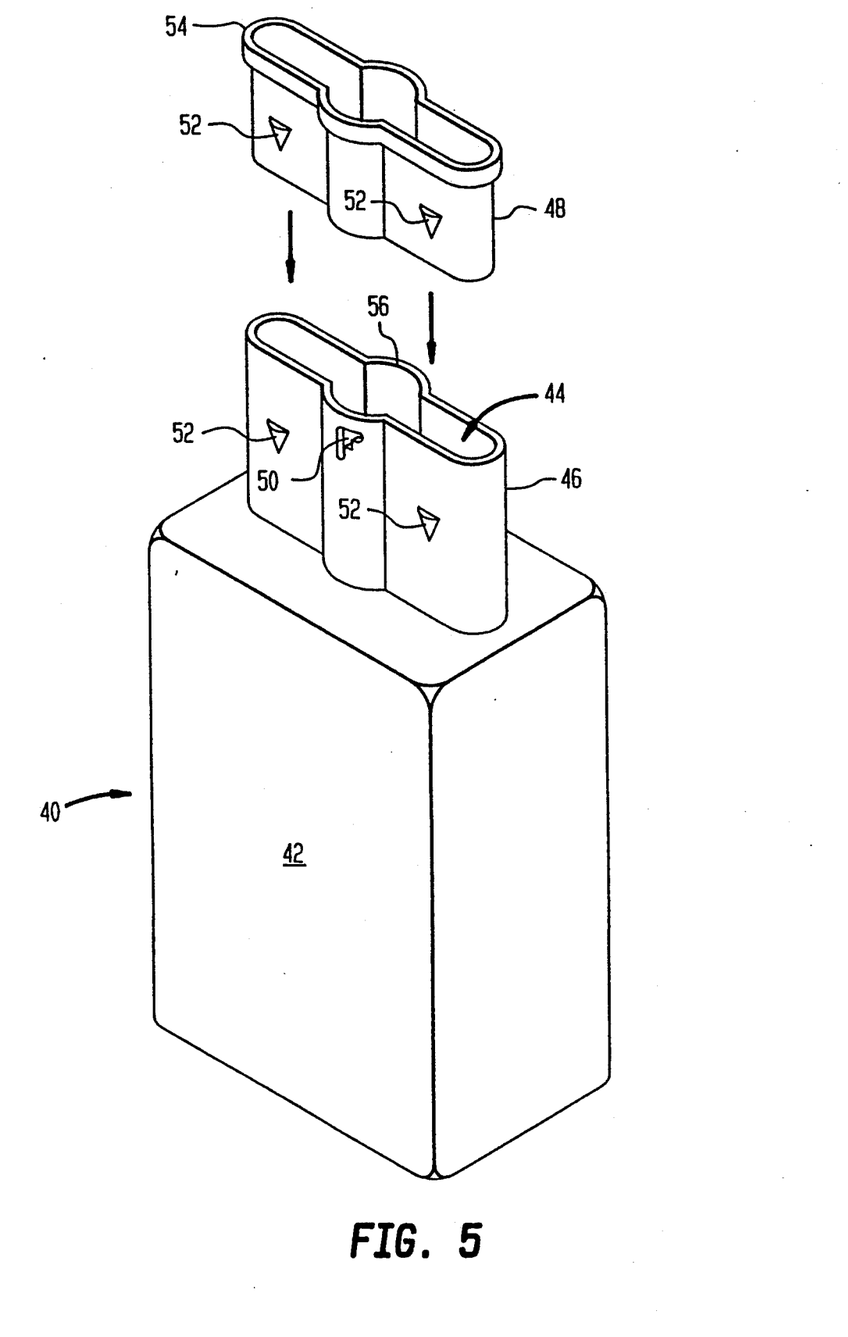
FIG. 5 is a schematic representation of a top-front perspective view of the inner container assembly of FIG. 4, wherein the aperture closure means has been removed therefrom and inverted such that it is ready to be inserted into the aperture and elongated neck portion for sealing of the inner container assembly.

The infectious waste disposal container assembly according to the present invention is shown in FIG. 4-7 attached hereto. FIG. 4 depicts an infectious waste disposal container assembly 40 which is inserted into the outer container assembly shown in FIGS. 1 and 2 via a hole created when the access door is in the open position. Container assembly 40 comprises a receptacle housing 42, an aperture 44 with elongated neck portion 46 and an aperture closure means 48. Aperture 44 is of sufficient dimensions to provide access by infectious wastes to the interior of receptacle housing 42. Aperture closure means 48 which is removed from container assembly 40 should be of a shape which permits its insertion into elongated neck portion 46 via aperture 44 when in its inverted position, thereby preventing infectious waste contained within receptacle housing 42 from escaping through aperture 44.

It is preferable that infectious waste disposal container assembly 40 with aperture closure means 48 be formed as a single blow molded piece, wherein aperture closure means 48 is removed following formation. That is, aperture closure means 48 may be cut along the "cut line" shown in FIG. 4 such that a lip 54 is formed which acts as a stopping means when aperture closure means 48 is inserted within elongated neck portion 46 such that it cannot pass completely through neck 46 into receptacle housing 42. As will be clearly understood by those skilled in the art, blow molding a single piece provides an extremely inexpensive means for forming complete container assemblies, i.e., it is not necessary to have two separate molds in order to form the container housing and the lid. Infectious waste disposal container assembly 40 is preferably formed from a high density polyethylene plastic, a polypropylene plastic, a styrene butadiene plastic or the like.

Optionally, elongated neck portion 46 may include a needle slot 50 disposed about at least one side wall thereof. It is preferable that needle slot 50 be disposed as close to the top of aperture 44 such that closure means 48 also acts to seal needle slot 50 when it is inserted into elongated neck portion 46.

Figure 7:
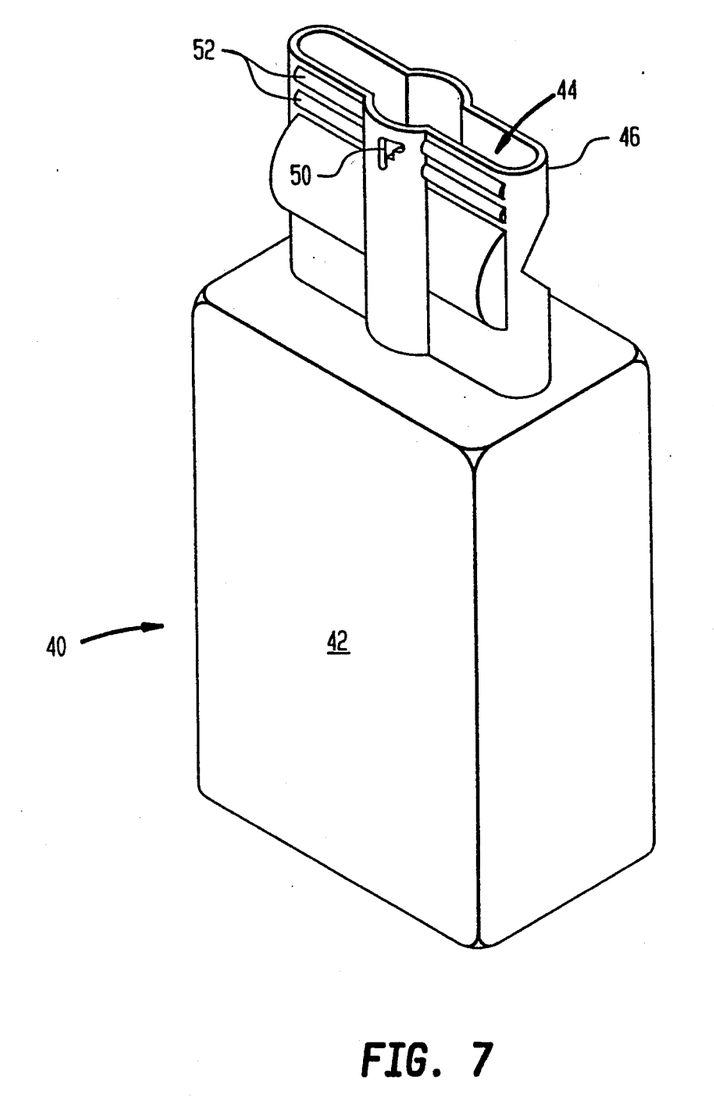
FIG. 7 is a schematic representation of a top-front perspective view of another embodiment of the inner container assembly wherein a V-shaped barrier means is molded into the elongated neck portion to restrict access to the receptacle housing.

Also, it is preferable that elongated neck portion 46 and aperture closure means 48 have at least one pair of adjacent mating snap locks 52. Snap locks 52 can be a pair of outwardly protruding molded dimples wherein a dimple molded in aperture closure means 48 fits securely within the interior of a dimple molded in elongated neck portion 46. It is, however, preferable that snap locks 52 be a pair of parallel, outwardly protruding ridges which extend along the entire length of opposing walls of aperture closure means 48 and elongated neck portion 46 as shown in FIG. 7. When snap locks 52 comprise a pair of parallel, outward protruding ridges the structural integrity of elongated neck portion 46 is enhanced. However, it should be clearly understood that snap locks 52 can be of any shape or size which provide a means for securely affixing aperture closure means 48 within the interior of elongated neck portion 46 such that infectious waste contained within receptacle housing 42 cannot escape via aperture 44.

Figure 6:
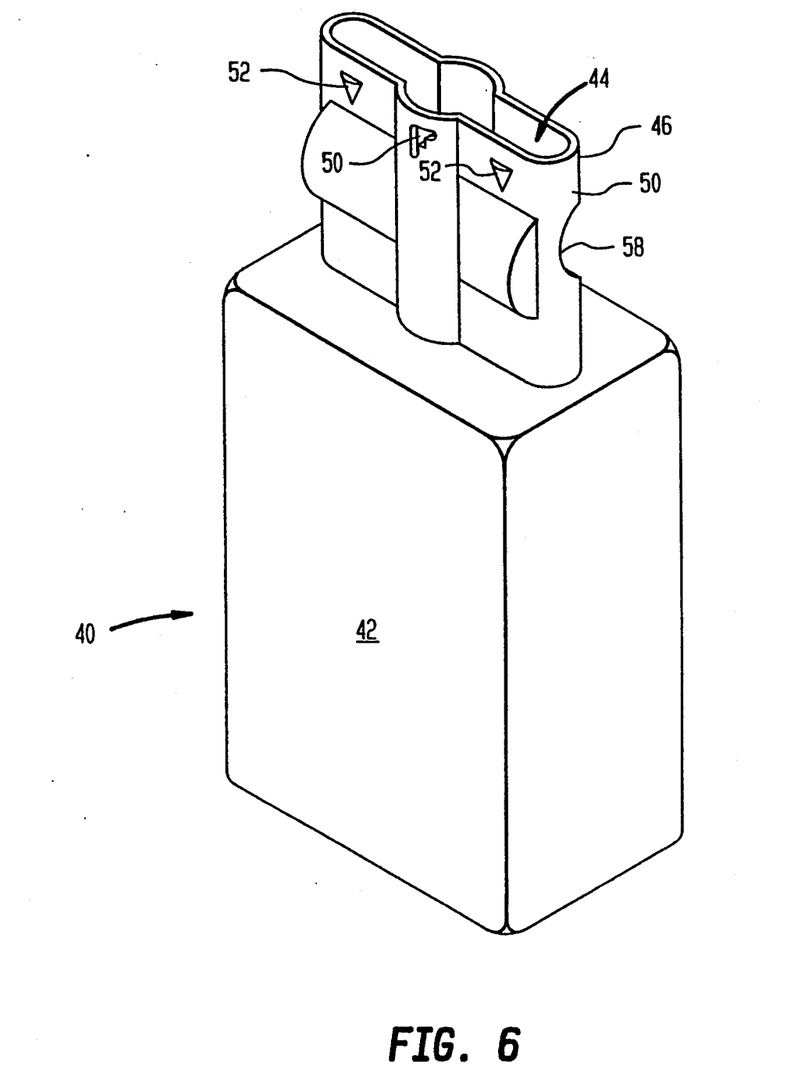
FIG. 6 is a schematic representation of a top-front perspective view of another embodiment of the inner container assembly wherein an arc-shaped or circular barrier means is molded into the elongated neck portion to restrict access to the receptacle housing.

Aperture 44 typically has either an oval or rectangular cross-section with a cylindrical conduit 56 disposed intermediate thereof. Optionally, elongated neck portion 46 comprises a barrier means 58 which is capable of restricting access to receptacle housing 42. That is, barrier means 58 is of a configuration such that it impedes access by human hands and the like into receptacle housing 42 while permitting infectious waste to pass there-through unimpeded. For example, FIG. 6 shows barrier means 58 as a horizontally disposed curved member molded together with elongated neck portion 46 and FIG. 7 shows barrier means 59 as a V-shaped member molded together with elongated neck portion 46.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. An infectious waste disposal system comprising:
an outer container assembly comprising a housing unit which comprises a front side wall, a rear side wall, a top portion, a base portion and a means for mounting said outer container assembly to a wall, an outer aperture disposed about said top portion of said housing unit, an access door disposed about said base portion of said housing unit and a means for locking said access door to said housing unit; and
a removable inner container assembly disposed within said outer container assembly, said inner container assembly comprising a receptacle housing, an inner aperture with an inner elongated neck portion and an aperture closure means, said inner aperture being capable of providing access to the interior of said receptacle housing and said aperture closure means having a shape such that it can be removed from said inner container assembly, inverted and inserted into said inner elongated neck portion via said inner aperture such that infectious waste container within said receptacle housing cannot escape through said inner aperture.

2. The system according to claim 1 wherein said mounting means is at least one through hole disposed within said rear side wall of said housing unit and a mechanical means for securing said outer container assembly to a wall or any other surface.

3. The system according to claim 2 wherein at least one slot corresponding to a respective through hole is disposed within said front side wall of said housing unit, whereby said mechanical means can be inserted within said slot such that it is in contact with said through hole.

4. The system according to claim 1 wherein said mounting means is an adhesive disposed upon the exterior surface of said rear side wall of said housing unit.

5. The system according to claim 1 wherein said inner container assembly is a single blow molded piece.

6. The system according to claim 5 wherein said inner container assembly is formed from a material selected from the group consisting of: a high density polyethylene plastic, a polypropylene plastic and a styrene butadiene plastic.

7. The system according to claim 1 wherein said inner elongated neck portion includes a needle slot disposed about at least one side wall thereof.

8. The system according to claim 1 wherein said inner elongated neck portion and said aperture closure means have at least one pair of adjacent mating snap locks.

9. The system according to claim 8 wherein said mating snap locks are outwardly protruding ridges which extend along the entire length of opposing walls of said aperture closure means and said elongated neck portion.

10. The system according to claim 1 wherein said inner aperture is oval in cross-sectional shape with a cylindrical conduit disposed intermediate thereof.

11. The system according to claim 1 wherein said inner elongated neck portion comprises a barrier means capable of restricting access to said receptacle housing.

12. The system according to claim 11 wherein said barrier means is a horizontally disposed curved member formed within said inner elongated neck portion.

13. The system according to claim 11 wherein said barrier means is a V-shaped member formed within said inner elongated neck portion.

14. The system according to claim 1 wherein said access door includes a locking device which is securely connected to a locking means disposed about said rear side wall of said housing unit when in the unopened position.

15. The system according to claim 14 wherein said means for locking said access door to said housing unit is a shelf molded into the lower portion of said rear side wall of said housing unit.

* * * * *